United States Patent [19]

Hochstrasser

[11] 4,059,407

[45] * Nov. 22, 1977

[54] DISPOSABLE CHEMICAL INDICATORS

[75] Inventor: Harry T. Hochstrasser, Hastings-on-Hudson, N.Y.

[73] Assignee: Becton, Dickinson and Company, Rutherford, N.J.

[*] Notice: The portion of the term of this patent subsequent to June 22, 1993, has been disclaimed.

[21] Appl. No.: 758,646

[22] Filed: Jan. 12, 1977

Related U.S. Application Data

[63] Continuation of Ser. No. 676,662, April 14, 1976, abandoned, which is a continuation-in-part of Ser. No. 533,972, Dec. 18, 1974, Pat. No. 3,964,871.

[51] Int. Cl.² ............................................. G01N 33/16
[52] U.S. Cl. .............................. 23/253 TP; 23/230 B; 195/103.5 C; 195/127
[58] Field of Search ................... 23/230 B, 253 TP; 195/103.5 R, 103.5 C, 127; 116/114 AM

[56] References Cited

U.S. PATENT DOCUMENTS

| | | |
|---|---|---|
| 2,464,155 | 3/1949 | Russell et al. ................. 23/253 TP |
| 2,799,167 | 7/1957 | Loconti ........................... 23/253 TP |
| 3,006,735 | 10/1961 | Jordan ............................ 23/253 TP |
| 3,036,894 | 5/1962 | Forestiere ....................... 23/253 TP |
| 3,050,373 | 8/1962 | Collins ............................ 23/253 |
| 3,139,328 | 6/1964 | Jacob ............................. 23/253 TP |
| 3,235,337 | 2/1966 | Artis ............................... 23/253 TP |
| 3,290,228 | 12/1966 | Gretton et al. ..................... 195/127 |
| 3,350,278 | 10/1967 | Gretton et al. ..................... 195/127 |
| 3,411,887 | 11/1968 | Ku ................................. 23/230 B |
| 3,453,180 | 7/1969 | Fraser, Jr. et al. ................ 23/230 B |
| 3,667,916 | 6/1972 | Sliva et al. ...................... 23/253 TP |
| 3,699,003 | 10/1972 | Kronish et al. ................... 23/253 TP |
| 3,810,739 | 5/1974 | Nussbaum ........................ 23/253 TP |
| 3,814,668 | 6/1974 | Blake et al. .................. 195/103.5 C |
| 3,964,871 | 6/1976 | Hochstrasser ................... 23/253 TP |

*Primary Examiner*—R.E. Serwin
*Attorney, Agent, or Firm*—Kane, Dalsimer, Kane, Sullivan and Kurucz

[57] ABSTRACT

A disposable indicator is disclosed which is useful for the measurement of ketones, proteins including albumin and uric acid in biological fluids. The instrument registers the concentration of substance in a given biological fluid with indicia which are directly readable in a convenient notation system (e.g., digital or other symbolic notation). The indicator comprises an improvement over prior art disposable devices which require a comparison of the viewable indication with a color intensity scale to translate the indicia registered to meaningful numerical values or other symbolic notations. The indicator permits the use of chemical reagent concentrations which are at least an order of magnitude greater than those used in prior art, thereby improving stability and drastically lowering the magnitude of interferences.

9 Claims, 10 Drawing Figures

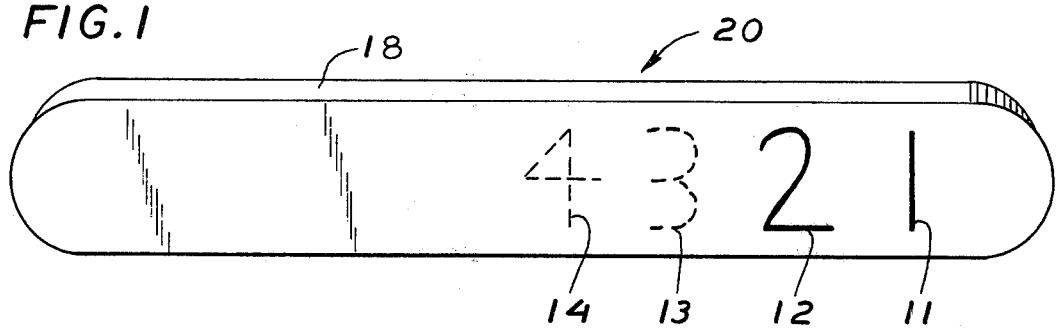
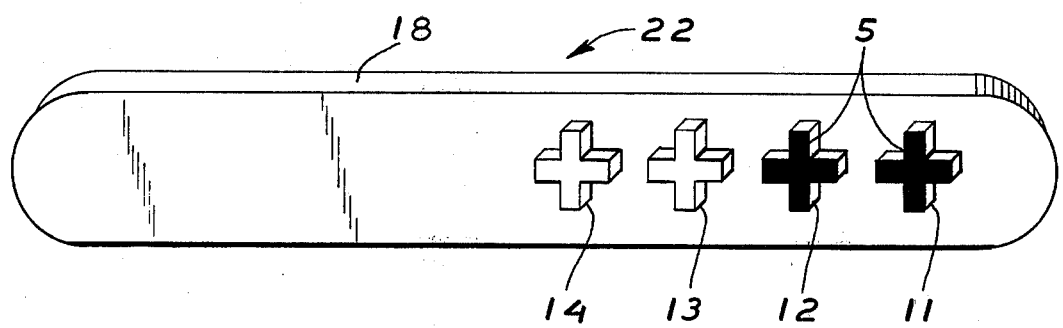
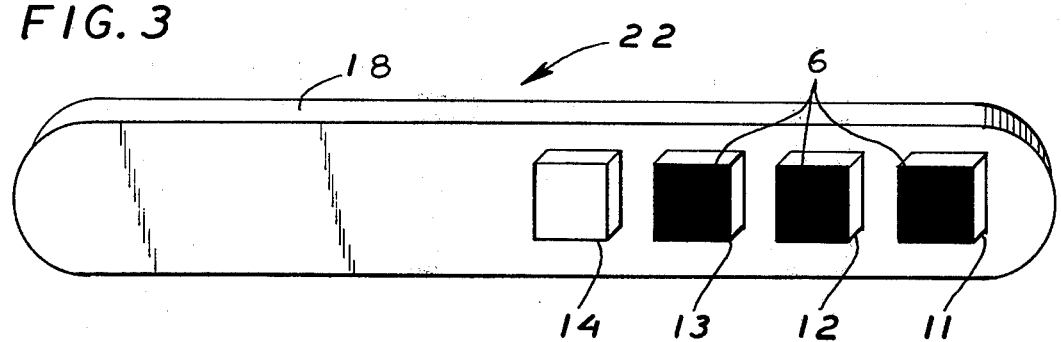
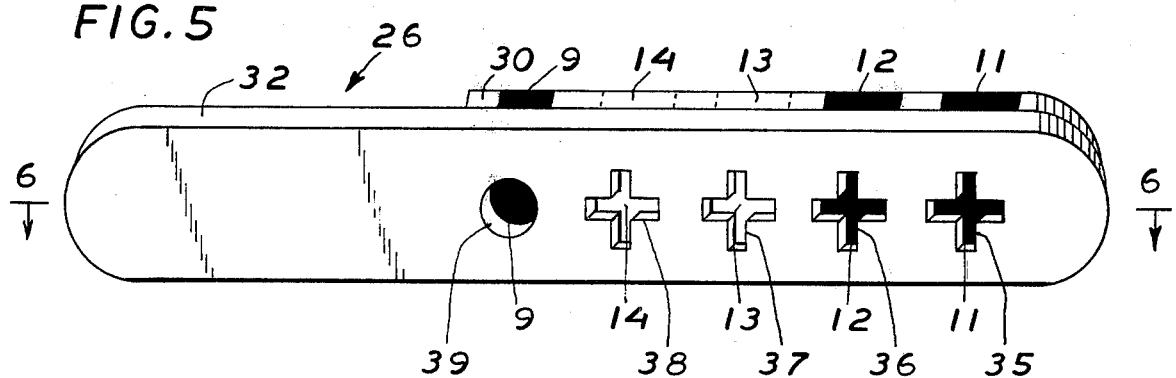

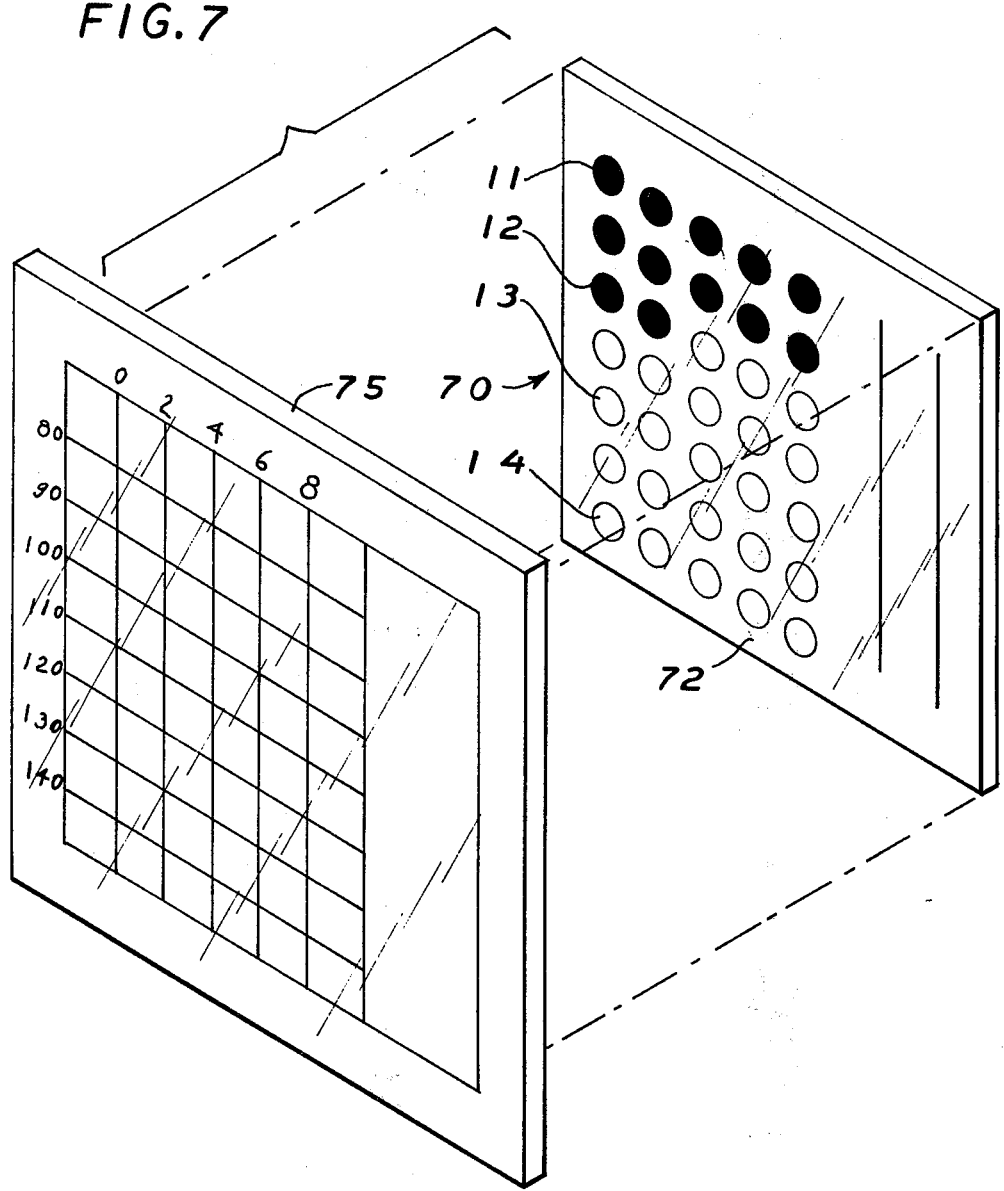

DISPOSABLE CHEMICAL INDICATORS

CROSS-REFERENCE TO RELATED APPLICATIONS

This application is a continuation of U.S. application Ser. No. 676,662 filed Apr. 14, 1976 and now allowed and, which in turn was a continuation-in-part of U.S. application Ser. No. 533,972 filed Dec. 18, 1974, and which has issued as U.S. Pat. No. 3,964,871.

BACKGROUND OF THE INVENTION

1. Field of the Invention

The invention concerns devices for the quantitative analysis of chemical substance concentrations in biological fluids.

2. Brief Description of the Prior Art

Prior hereto, disposable devices have been known and commercially available which are useful for determining the concentration of glucose (and other substances) in liquids. Of particular importance for their simplicity, low cost, ease of operation and widespread use are the relatively simple devices which comprise a strip of bibulous material or other support element bearing a reagent which yields a color indication upon contact with glucose. Representative of such devices are the devices described in U.S. Pat. Nos. 2,865,718; 2,848,308; 2,893,844; 2,981,606; 3,164,534; 3,212,855; and 3,791,988. For substances other than glucose see: U.S. Pat. Nos. 3,012,976; 3,092,463; 3,252,762; 3,290,117; 3,095,277;, 3,438,737; 3,212,855; 3,050,373; 3,123,443; 3,122,420; 3,453,180; 3,585,001; 3,585,004; and 3,447,905.

The devices described in the above prior art patents all operate by immersion in e.g. a chemical substance containing solution for brief periods of time. On contact with the chemical substance, the reagent element of the device undergoes a chemical change, which is indicated visually to the operator by a color change. Generally, the degree of color change is a crude measure of the concentration of chemical substance in the immersion liquid. For example, the device of U.S. Pat. No. 2,981,606 employs a reagent composition which gives a color indication, depending on the concentration of glucose in the immersion liquid, varying from tints of yellow to green to blue. An approximation of the glucose content of the immersion solution in terms of percentage is then obtained by comparing the color indication with color shades obtained by exposure of the reagent to solutions of known glucose content. In practice, a secondary color comparison chart is used.

Other devices of the prior art employ a single reagent which is sensitive to, for example, glucose above a specific concentration. These latter devices, as represented by the devices disclosed in U.S. Pat. No. 2,893,844, also give the operator a visual indication by color formed upon reaction of the reagent element with glucose. The devices to not indicate a range of concentrations, but only indicate if a certain predetermined level of glucose is present or exceeded in the solution being tested.

The disposable devices of the prior art have not offered a means of obtaining a direct numerical reading of glucose or other substance content of the tested solutions. For this determination, either a comparison with a color chart must be made to convert the indicia registered by the device to a numerical value or multiple tests would have to be carried out using a separate indicator device for a number of different minimum glucose level determinations. Both devices offer only a crude approximation of glucose concentrations and are dependent upon the ability of the user of the device to differentiate shades of colors.

A further disadvantage of the commercially available prior art devices resides in the fact that they must be employed following closely defined operating rules. More particularly, the reagents employed continue to react after initial contact with the substance to be detected, such as glucose. The colors formed by the reagents continue to develop to the darkest shade possible and so the indicator must be read within a narrow and specific time period following immersion if any accuracy is to be obtained in the determination. If the operator fails to understand the criticality involved in reading the indicia registered within the prescribed time, or fails to do so accurately, an erroneous reading will be obtained. The indicators of my invention are disposable, register an indicia of dissolved substance concentration which is directly readable in numerical terms and will indicate over any desired range of possible concentrations. In addition, the indicators of my invention provide a registration soon after brief immersion in the containing solution and do not have to be "read" within a critical time period following such immersion. The indicia registrations obtained are stable for reasonably long periods following exposure (particularly to glucose) so that a degree of freedom is obtained as to when the registration must be observed for an accurate reading.

Furthermore, instruments of my making, prepared according to the invention are comparatively insensitive to the effects of interfering substances in the test specimens. This leads to the creation of potential gross errors in diagnosis and to the erroneous administration or withholding of certain therapeutic drugs. In using the instruments and reagent formulations of my invention however, the effects of such interferences are virtually eliminated, i.e. reduced to about 3% of the effect seen with prior art instruments.

SUMMARY OF THE INVENTION

The invention comprises an indicator for the measurement of chemical substances dissolved in biological fluids, which comprises; a support member; and a plurality of indicating reagents for said substances, each of which is located in a separate zone of said member and at least two of which indicate the presence of a different concentration of said substance in solution, by causing the registration of convenient symbols, including digits.

The invention also comprises a method of determining the concentration of a chemical compound in a solution, which comprises; immersing an instrument of the invention in the compound containing solution, removing said instrument from said solution and reading the indicated concentration of the chemical substance directly from the instrument.

BRIEF DESCRIPTION OF THE DRAWINGS

FIG. 1 is an isometric view of an indicator embodiment of the invention, following use in a solution containing a chemical substance.

FIG. 2 is an isometric view of an alternate indicator embodiment of the invention after use.

FIG. 3 is a isometric view of another embodiment of the invention after use.

FIG. 5 is an isometric view of a preferred indicator embodiment of the invention shown after use.

FIG. 7 is an isometric view of an alternate embodiment of the invention.

DETAILED DESCRIPTION OF THE INVENTION

Figure 6:
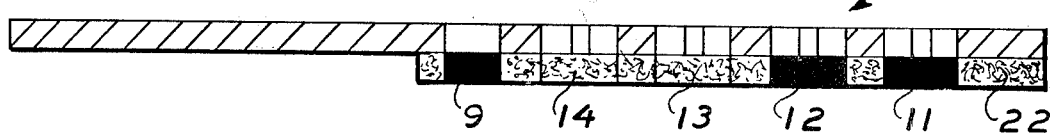
FIG. 6 is a cross-sectional longitudinal view along lines 6—6 of FIG. 5.

The indicators of the invention are relatively simple devices which may be used once and thereafter disposed of. For this reason they may be termed "disposable" instruments. The indicators of the invention may be employed to determine the presence and concentration of any chemical substance in any biological fluid. For example, by the selection of appropriate reagents, the indicator devices of the invention may be employed to determine the concentration of protein
albumin
ketones
bilirubin
blood
hemaglobin
urobilinogen
nitrates
nitrites
antigens
antibodies
digoxin
digitoxin
hepatitis B antigen
thyroxine
triiodothyronine
cholesterol
uric acid
lactic acid
creatinine
triglycerides
urea
glutamic-oxaloacetic transaminase
glutamic-pyruvic transaminase
lactic acid dehydrogenase
hydroxybutyric acid dehydrogenase
alkaline phosphatase
acid phosphatase
amylase
lipase
creatine phosphokinase and the like, in biological fluids.

The indicator devices of the invention are particularly useful for detecting organic chemical substances.

The indicators of the invention comprise a support member bearing a plurality of specific reagents. The support member is not critical in the sense that a specific material of construction is required although several forms of the preferred embodiments will be described hereinafter. In general, the support member may be of any material capable of bearing the reagent for exposure to the solution to be tested. Specific examples of support members are webs, sticks, strips, splinters, sheets, rods and like forms of glass, metal, wood, paper; polymerics such as polyethylene, polypropylene, polyalkylene acetate, polycarbonates and the like; textiles and the like. Preferred materials are the bibulous materials which may be impregnated with solutions of reagent compositions, such as filter papers, blotting papers and like bibulous materials.

The reagent components of the indicators of the invention are preferably prepared in a liquid form for deposit upon the support member. Once placed on the support member, the reagent compositions in solution are dried to adhere the compositions to the support member. Generally, adhesion of the reagent compositions to the support member is conveniently effected when the support member is a bibulous material. Conventionally employed inert fillers, binders, surfactants and the like may be incorporated into the reagent compositions when desired. Certain binders such as resin gums are advantageously incorporated into the reagent compositions to assist in adhering them to non-porous support members such as metal, glass or non-porous polymeric materials. For product elegance, it is desirable that the color change in each indicator zone of the devices of the invention be clear, sharp, unequivocal and strongly positive. I have found that the degree of accuracy and precision with which the devices of the invention function in accord with this desire is related to the ratio of volume of reagent solution deposited on the support member to volume of reagent solution deposited on the support member to volume of test solution absorbed at the reagent site during immersion in the test solution or biological fluid. The most advantageous device of the invention in terms of accuracy and precision obtainable are those wherein the above described ratio is substantially a 1:1 ratio. The further one departs from this optimum ratio, the greater will be the loss of accuracy and precision in the indicator devices.

Upon immersion in the biological solution being tested, the bibulous material at the site of reagent deposition will generally take up a volume of the test solution which is equivalent to the volume of solvent evaporated resulting in the desired 1:1 ratio described above. However, unless the area of reagent impregnation is isolated in a manner so as to provide a site of precise and determinable volume, the reagent may be carried beyond the site of original deposition upon immersion in the test solution. This will result in dilution of the reagent in terms of its proportion in the absorbed test solution during the test procedure, and ultimately results in a variation from the desired 1:1 ratio described above. Therefore, preferred devices of the invention wherein the indicator reagent is carried on a bibulous material preferably have the plurality of indicator reagent sites separated from each other by a non-absorbent or hydrophobic material and each site preferably will absorb nearly identical volumes of the solvent employed in depositing reagent and of the biological fluid to be tested. The preferred device may be prepared, for example, by affixing a plurality of the reagent impregnated bibulous support members (each bearing a reagent of different sensitivity to the substance being tested for, as described more fully hereinafter) to a different zone of a hydrophobic support member such as a polymeric resin solid strip like polyethylene, polypropylene, etc. Upon immersion of such a device in the test solution, a precise volume of the test fluid is absorbed at the site of the indicator reagent which is then diluted accurately to substantially the same concentration at which it was deposited in the deposition solvent employed in preparing the indicator reagent site. Illustrative of such preferred indicator devices are those described more fully hereinafter, particularly the embodiment of FIGS. 2 and 3.

The reagent components of the indicators of the invention may be any of the known reagents for the quantitative detection of the substance being analyzed for, and which will give a visual indication when exposed to specific concentrations of such substance in a solution thereof. A plurality of such reagents are placed on the support member, each in a different zone of the member and at least two of said reagents providing an indication of different substance-in-solution concentration levels. Such reagents and the means for their preparation are generally known. Preferred reagents are those which comprise a specified amount of a titrant which reacts with one of the products in the series of reactions starting with the constituent being analyzed and proceeding to completion with the formation of one or more products, one of which reacts quantitatively with the titrant, and is thus not permitted to accumulate until all of the titrant is consumed, at which time the accumulation of said product becomes visible to the eye, or to a photoelectric sensor device, by virtue of either its native color or by virtue of its reaction with a suitable indicator eye. Representative of such titrations and the reagent systems which provide the desired indications are the following, wherein a titration of the constituent analyzed for (hereinafter referred to as the analyte) is made against a chemical reducing compound.

Scheme 1-A

1. Analyte + $O_2$ $\xrightarrow{\text{Catalyst A}}$ $H_2O_2$

2. $H_2O_2$ + reduced indicator $\xrightarrow{\text{Catalyst B}}$ oxidized indicator.

3. Oxidized indicator + titrant $\longrightarrow$ reduced indicator (oxidized, e.g. colored, indicator does not accumulate until all of titrant has been consumed).

Specific Scheme I-A Examples:

| | Reagent Composition | | | |
|---|---|---|---|---|
| | Auxiliary Reagents | | | |
| Analyte | Catalyst A | Catalyst B | Indicator | Titrant |
| cholesterol | cholesterol oxidase | peroxidase | red-ox dye | Reductant |
| cholesterol | cholesterol oxidase | peroxidase | ABTS* | Reductant |
| cholesterol | cholesterol oxidase | peroxidase | o-dianisidine | Reductant |
| cholesterol | cholesterol oxidase | peroxidase | p-diphenylamine sulfonic acid | Reductant |
| cholesterol | cholesterol oxidase | peroxidase | red-ox dye | Ascorbic acid |
| cholesterol | cholesterol oxidase | peroxidase | ABTS* | Ascorbic acid |
| cholesterol | cholesterol oxidase | peroxidase | ABTS* | Gentisic acid |
| Uric acid | Uricase | peroxidase | red-ox dye | Reductant |
| Uric acid | Uricase | peroxidase | ABTS* | Reductant |
| Uric acid | Uricase | peroxidase | o-dianisidine | Reductant |
| Uric acid | Uricase | peroxidase | p-diphenylamine sulfonic acid | Reductant |
| Uric acid | Uricase | peroxidase | red-ox dye | Ascorbic acid |
| Uric acid | Uricase | peroxidase | ABTS* | Ascorbic acid |
| Uric acid | Uricase | peroxidase | ABTS* | Gentistic acid |

*ABTS is 2.2'-azino-di-(3-ethyl-benzothiazoline-6-sulphonic acid.
NOTE: In any of the above, the red-ox dye may be any compound oxidizable by $H_2O_2$ (plus peroxidide) which is reconverted to reduced form by titrant (reductant) and is visibly colored in either, but not both, of its reduced and oxidized forms.

Similarly, the titrant (reductant) may be any compound that rapidly converts the oxidized red-ox dye to its reduced form, and should itself be essentially colorless to the eye.

SCHEME I-B

1. Analyte + reagent + reduced indicator→Oxidized Indicator
2. Oxidized indicator + titrant→reduced indicator Specific I-B Examples:

| Analyte **** | Reagent | Indicator | Titrant |
|---|---|---|---|
| Hemoglobin | Organic peroxide * | Ox-red indicator ** | reductant *** |
| Peroxidase **** | " | " | " |
| Blood **** | " | " | " |
| Glutamic-pyruvic transaminase | alanine alpha-ketoglutarate lacticdehydrogenase reduced nicotinamideadenine dinuclectide (NADH) | " | " |
| Glutamic-oxaloacetic transaminase | aspartic acid alpha-ketoglutaric acid malic acid dehydrogenase (NADH) | " | " |

* organic peroxides:
    Cumene hydroperoxidez****
** Indicators:
    o-dianisidine
    p-toluidine
    ABTS (supra)
    p-diphenylamine sulfonic acid
    o-tolidine
    neutral red (cert.)
    janus green B (cert.)
    2,6-dibromoindophenol sodium salt (pract.)
    N,N-dimethylindoaniline (pract.)
**** See U.S. Pat. Nos. 3,012,976; 3,092,463 3,252,762; and 3,290,117.
    Indophenol sodium salt (pract.)
    2,3',6-trichloroindophenol sodium salt (pract.)
    phenosafranine
    5,5'-indigodisulfonic acid disodium salt (pract.)
    nile blue A (cert.)
    methylene blue (cert.)
    thionin (cert.)
    brilliant cresyl blue (cert.)
    2,6-dichloroindophenol sodium salt
    N-(p-methoxyphenyl)-p-phenylene-diamine hydrochloride
    3,3'-dimethoxybenzidine (pract.)
    3,3'-dimethoxybenzidine dihydrochloride
    N,N-dimethyl-p-phenylenediamine (pract.)
    N,N'-diphenylbenzidine (pract.)
    diphenylamine
    4-(p-ethoxyphenylazo)-m-phenylenediamine monohydrochloride
    p-diphenylaminesulfonic acid sodium salt
    barium diphenylaminesulfonate
    o-tolidine
    xylene cyanole FF (techn.)
    N-phenylanthranilic acid
    tris (1,10-phenanthroline)iron(II) sulfate solution
    dicyanobis (2,2'-bipyridine) iron
    dicyanobis (1,10-phenanthroline) iron
    benzopurpurin 4B
    naphthol blue black
*** Titrants:
    Gentisic acid
    Ascorbic acid
    Hydroquinone
    Pyrogallol
    Hydroxylamine
    sodium nitrite
    sodium bisulfite
    sodium thiosulfate
    cysteine
    hydrazine
    ferrous ion, and complexes thereof
    cuprous ion, and complexes thereof

| Examples | | | |
|---|---|---|---|
| Analyte | Auxiliary Reagents | Indicator | Titrant |
| Lactic acid | lactic acid | Ox-red | Oxidant |

-continued

|  | dehydrogenase | indicator | (list) ** |
|---|---|---|---|
|  | NAD (nicotinamide adenine dinucleotide) | (list) * |  |
| Lactic acid dehydrogenase | lactic acid NAD | " | " |
| Triglycerides | lipase glycerol dehydrogenase NAD | " | " |
| Hydroxybutyric acid dehydrogenase | hydroxybutyric acid NAD | " | " |

\* Indicator List:
  same as I-B above.
\*\* Oxidant List:
  1. cumene hydroperoxide + horse radish peroxidase (auxiliary reagent)

SCHEME III

Compositions that effect a titration of the analyte against specific complexigenic compounds or substances.

SCHEME III-A

Compositions in which titrant forms an unreactive complex with analyte, thus preventing reaction of analyte with auxiliary reagents unless analyte concentration exceeds complexigenic compound concentration.

Examples:

| Analyte | Titrant | Auxiliary Reagents |
|---|---|---|
| Ketones \*\* | sodium bisulfite | sodium nitroprusside glycine |
| Proteins \*\* | sodium salycilate | tetrabromophenol |
| " | sodium dodecyl sulfonate | " |
| Albumin | sodium salycilate | brom cresol green |
| " | sodium dodecyl sulfonate | " |
| " | sodium salycilate | o((p-hydroxyphenyl)azo)-benzoic acid |
| " | sodium dodecyl sulfonate | " |
| Bilirubin | simple aldehydes | dichloroaniline diazonium salt |
| " | benzaldehyde | " |
| Urobilinogen \*\*\* | simple aldehydes | p-dimethylamino-benzaldehyde |
| " | benzaldehyde | " |

\* See U.S. Pat. No. 3,212,855
\*\* See U.S. Pat. Nos. 3,095,277 and 3,438,737.
\*\*\* See U.S. Pat. Nos. one or more of following: 3,050,373; 3,123,443; 3,122,420; 3,453,180; 3,585,001; 3,585,004; and 3,447,905.

SCHEME III-B

Compositions in which analyte reacts with a specific binding substance (titrant) and renders at least a portion of said substance undetectable by a subsequent indicating auxiliary reagent.

GENERAL SCHEME: (III-B)

Reagent zones each contain a different amount of titrant. Upon exposure to biological fluid, containing analyte, one or more zones will be completely reacted with analyte, and will be unable to react with subsequent indicator reagent. For fluids containing low concentrations of analyte, many or all zones will remain detectable. For fluids containing large quantities of analyte, most or all zones will be rendered non-detectable.

Specific Examples of III-B:

| Analyte | Titrant | Indicator Reagent(s) |
|---|---|---|
| 1. Antigen | antibody | labeled antigen |
| " | " | radioactive antigen |
| " | " | enzyme-labeled antigen plus appropriate substrates to generate a colored product |
| 2. " | " | horseradish peroxidase-labeled antigen, cumene hydroperoxide, ABTS (supra) |
| 3. " | " | horseradish peroxidase-labeled antigen, sodium perborate, ABTS (supra) |
| 4. Ligand | specific-ligand-binding protein | same as 1 above, but substitute "ligand" for "antigen" |
| 5. " | " | same as 2 above, substituting again |
| 6. " | " | same as 3 above, substituting |

NOTE: Relative to III-B example, enzyme labels in such assays are well known; see for example U.S. Patent Nos. 3,791,932; 3,839,153; and 3,850,752. In these patents the claims all relate to methods dependent upon measuring the amount of enzyme label found after certain separation procedures. In my invention, I do not measure amounts of enzyme label, but only use it as a gross indicator of whether or not all antibody combining sites have been reacted.

The following examples describe the manner and process of making and using this invention and set forth the best mode contemplated by the inventor of carrying out the invention but are not to be construed as limiting. All parts are by weight unless otherwise indicated.

EXAMPLE I

A. To an appropriate vessel there is charged 300 microliters of a solution of cholesterol oxidase (1.0 IU/ml, in phosphate buffer 0.1M, pH 7), 300 microliters of solution of cholesterol esterase (1.0 IU/ml in phosphate buffer, pH 7), 150 microliters of a solution of horseradish peroxidase (30,000 IU/ml in 0.01M phosphate buffer, pH 7), 300 microliters of 2,2'-azino-di-(3-ethyl-benzothiazoline-6-sulphonic acid) in solution [prepared by dissolving 50 milligrams of 2,2'-azino-di-(3-ethyl-benzothiazoline-6-sulphonic acid) (Boehringer Manneheim Corporation, New York, New York, product No. 15594) in 1.0 milliliters of 0.1M phosphate buffer (pH 7)] and 0.1M phosphate buffer (pH 7) quantum sufficient to make a total of 1,250 microliters. The mixture is thoroughly admixed to obtain a cholesterol indicating reagent solution.

B. In an appropriate vessel 0.5 grams of 2,5-dihydroxybenzoic acid is slurried in 4 milliliters of water. To the slurry there is then added with stirring a solution of 10% sodium hydroxide in water until a clear solution is obtained. This is used as a stock 10% solution. A working 1% solution is prepared by appropriate dilution with 0.1M phosphate buffer (pH 7).

C. Four separate appropriate vessels are each charged with 80 microliters of the indicating reagent solution prepared in (A) above. In each vessel there is then added with mixing, various proportions of the 1% 2,5-dihydroxybenzoic acid solution prepared in (B), supra, and varying amounts of buffer as described in (A) above to obtain cholesterol indicating reagent solutions, each of which will indicate visually when exposed to various minimum concentrations of cholesterol in solution, by a color change of from substantially colorless to colored. The four vessels are identified by the letters A through D inclusive. The concentration of 2,5-dihydroxybenzoic acid and buffer in each vessel and the minimum cholesterol concentration of a solution which each reagent composition A through D inclusive will indicate by a color change are shown in Table I below.

TABLE I

| Vessel | Buffer (Microliters) | 2,5-DHBA (Microliters) | Concentration of 2,5-DHBA | Percent of Minimum Cholesterol Concentration in Solution Required for Indication to Occur |
|---|---|---|---|---|
| A | 12 | 8 | 80 mg/dl | 200 mg/dl |
| B | 8 | 12 | 120 mg/dl | 300 mg/dl |
| C | 4 | 16 | 160 mg/dl | 400 mg/dl |
| D | 0 | 20 | 200 mg/dl | 500 mg/dl |

Similarly, following the procedure of Example I, part A above, but replacing the 2,5-DHBA as used therein with an equivalent proportion of indoxyl sulfate; Uric acid; 3,4-dihydroxymandelic acid; 3-methoxy-4-hydroxymandelic acid; 3,4-dihydroxyphenylacetic acid; 3-methoxy-4-hydroxyphenylacetic acid; 3,4-dihydroxyphenylalanine; 3-methoxy-4-hydroxyphenylalanine; 5-hydroxyindole-3-acetic acid; 5-hydroxyindole-2-carboxylic acid; 5-hydroxytryptophane; creatinine; 2,5-dihydroxyphenylacetic acid; o-hydroxytramine (dopamine); and 5-hydroxytryptamine, respectively, cholesterol indicating reagent solutions may be obtained which are useful in fabricating indicator devices of the invention.

EXAMPLE II

A series of five sets of circular discs are prepared, each set consisting of four discs and each disc being fashioned from #52 Whatman filter paper by cutting out a circle, 4 mm, in diameter. Each disc within each set is then wetted with about 0.002 ml of a different one of the reagent solutions A, B, C and D, respectively, prepared in Example I, supra. The wet discs are allowed to air-dry. Each disc is calculated to contain, on drying, approximately 0.00038 IU of cholesterol oxidase, 0.00038 IU cholesterol esterase, 5.6 IU of peroxidase, 19.2 micrograms of 2,2'-azine-di-(3-ethyl-benzothiazoline-6-sulphonic acid) and varying proportions of 2,5-dihydroxybenzoic acid. The dry discs of each set are then mounted on a single paper strip, and each disc labeled a, b, c or d to correspond to the particular reagent A, B, C and D, respectively, employed in its preparation. Four of the paper strips each bearing a separate set of the four discs a-d is then immersed in one of four aqueous solutions containing 200, 300, 400, and 500 mg/dl cholesterol respectively. The fifth strip is a control strip and is immersed in distilled water. Each strip is immersed in the solution for a period of about one second and then withdrawn. Each strip is observed for a change of color in the discs mounted thereon as an indication of the presence or absence of cholesterol. The expected results are given in Table II below, with the proportion of 2,5-dihydroxybenzoic acid calculated to be present in each disc.

TABLE II

| Strip No. | % of Cholesterol in Immersion Solution | Disc | Proportion of 2,5-dihydroxybenzoic Acid (mcg) per disc | Color Change |
|---|---|---|---|---|
| 1 | 200 mg/dl | | | |
| | | a | 1.6 | Yes |
| | | b | 2.4 | No |
| | | c | 3.2 | No |
| | | d | 4.0 | No |
| 2 | 300 mg/dl | | | |
| | | a | 1.6 | Yes |
| | | b | 2.4 | Yes |
| | | c | 3.2 | No |
| | | d | 4.0 | No |
| 3 | 400 mg/dl | | | |
| | | a | 1.6 | Yes |
| | | b | 2.4 | Yes |
| | | c | 3.2 | Yes |
| | | d | 4.0 | No |
| 4 | 500 mg/dl | | | |
| | | a | 1.6 | Yes |
| | | b | 2.4 | Yes |
| | | c | 3.2 | Yes |
| | | d | 4.0 | Yes |
| 5 (Control) | 0.0% | | | |
| | | a | 1.6 | No |
| | | b | 2.4 | No |
| | | c | 3.2 | No |
| | | d | 4.0 | No |

Similarly, following the general procedure outlined above, but employing the reagents described above for the quantitative analysis of any of the following chemical substances:

protein
albumin
ketones
bilirubin
blood
hemoglobin
urobilinogen
nitrates
nitrites
antigens
antibodies
digoxin
digitoxin
hepatitis B antigen
thyroxine
triiodothyronine
uric acid
lactic acid
creatinine
triglycerides
urea
glutamic-oxaloacetic transaminase
glutamic-pyruvic transaminase
lactic acid dehydrogenase
hydroxybutyric acid dehydrogenase
alkaline phosphatase
acid phosphatase
amylase
lipase
creatine phosphokinase their determinations in a biological fluid may be determined.

The indicator of the invention and the method of the invention will now be further illustrated by reference to the specific embodiments shown in the accompanying drawings.

In FIG. 1 there appears a perspective view of an indicator 20 of the invention. The indicator 20 comprises a support member which is shown in FIG. 1 as a flat strip 18 and which preferably is bibulous material such as an absorbent paper strip. Disposed on the strip 18 by impregnation thereon in a manner so as to form the numerals 1, 2, 3, and 4 are reagents 11, 12, 13 and 14 respectively. Reagent 11 is a composition such as composition A of Example I, supra. and will indicate by color change when a minimum cholesterol concentration of 0.2% is present in a solution brought into contact with the reagent. Reagents 12, 13 and 14 correspond to the reagent compositions B, C and D respectively of Example I, supra. and will indicate the minimum cholesterol concentrations of 0.3%, 0.4% and 0.5% in cholesterol containing solutions, respectively. The disposition of the reagent compositions on the support member 18 may of course be in any convenient indicia. For example, the minimum concentration indicated by a given reagent may be the form of disposition, i.e.; for example, reagent 11 above described may be disposed in the configuration "0.2%". The numerals 1, 2, 3 and 4 selected for illustration of FIG. 1 is especially useful when the indicator device is to be employed for determining the chemical concentration in broad ranges. Such indicia conform to the to the practice of referring to a 0.2% concentration as a "plus 1" level, a 0.3% concentration as "plus 2", a 0.4% concentration is "plus 3" and a 0.5% concentration as "plus 4".

Prior to use, the symbols 1, 2, 3 and 4 employed in the embodiment of FIG. 1 may be invisible to view or only slightly decipherable through a slight discoloration upon strip 18. The broken lines indicating the numerals 3 and 4 are intended to show that the numerals 3 and 4 are not clearly decipherable as originally formed on member 18. Upon exposure however to a chemical solution by immersion therein, the reagents react chemically to produce a color. If the chemical concentration in the tested solution exceeds the minimum concentration for which the reagent will give a color indication, such color change occurs. In the FIG. 1 numerals 1 and 2 are shown in distinct dark tones and illustrate the indication obtained following immersion of indicator 20 in a solution of a chemical containing a chemical concentration of from between 0.3% and 0.4%. Reagents 11 and 12 have reacted to indicate a "plus 2" concentration, i.e.; the highest number developed. The development of reagents 11 and 12 to produce a clear and distinct color change forming distinct solid numerals gives a direct reading to the user of the minimum chemical concentration in the solution tested. Thus, the method of the invention is carried out by immersing that portion of indicator 20 which bears reagents 11, 12, 13 and 14, into a chemical containing solution momentarily, withdrawing it and visually observing the indicia registered. It will be observed that the operator does not have to carry out a comparison of colors registered, with standard charts to determine the concentration of the tested solution, as is necessary with prior art disposable devices. When the preferred composition of the invention is employed as the reagents 11, 12, 13 and 14, clear and distinct indications of concentration are obtained within about one minute. The indicia registered on the indicator are relatively stable and will last for a relatively long time so that at an interval of up to at least 72 hours after immersion and withdrawal of indicator 20, the user may refer back to recheck the test results. This is not possible with prior art devices.

The embodiment illustrated in FIG. 1 may obviously be modified in many respects to meet specific needs. The degree of sensitivity of each reagent may be modified to meet specific needs. Different ranges and sensitivities of the indicator devices may be obtained by selection of the reagent sensitivities and the number of different reagent compositions applied to the support member. The support member, strip 18 may also be dyed a particular color to either blend with the reagent compositions prior to their indicating the presence of chemicals or they may be dyed a color to provide a very sharp contrast when the reagent reacts to produce a registration.

As further examples of modifications which may be made to the basic indicator shown in FIG. 1, reference is now made to FIG. 2 which shows an isometric view of indicator 22 which may also comprise a support member 18 as described above and upon which there have been mounted "plus-shaped" blocks 5 of a bibulous material. Each block 5 has been saturated with a solution of a reagent 11, 12, 13 and 14 respectively as described above in conjunction with FIG. 1 and then dried before fixation upon support member 18. When indicator 22 is immersed briefly in a chemical containing solution the reagents carried on blocks 5 react as described above, and if the chemical level exceeds the minimum indicating sensitivity of the particular reagent, a color change in the block 5 carrying that reagent is visually observable. By counting the "pluses" which have changed color, the operator can read the device directly. In the device 22, as shown, a "plus 2" has been indicated, i.e.; the device was exposed to a solution containing between 0.3% and 0.4% of, for example, cholesterol.

FIG. 3 is an alternate embodiment similar to device 22 of FIG. 2, differing essentially in that the shape of the bibulous block 6 is a rectangle rather than a cross. This embodiment is operated in the same way as the device of FIG. 2 and as shown here has been exposed to a solution of a chemical in the "plus 3" concentration range, i.e.; the solution tested had a chemical concentration of between 0.4% to 0.5%.

The embodiment of FIGS. 2 and 3 are particularly advantageous when the support member 18 is a hydrophobic material such as, for example, polyethylene. The blocks 5 and 6 will each then absorb a predetermined volume of the biological fluid being tested, upon immersion. When the indicator reagents 11, 12, 13 and 14 have been deposited on blocks 5 and 6 by saturation of said blocks 5 and 6 with the indicator reagents 11, 12, 13 and 14 in solution followed by evaporation of the reagent solvent, the volume of test solution absorbed in blocks 5 and 6 on immersion in test solution will be substantially equal to the volume of solvent evaporated from the blocks 5 and 6 to deposit the indicator reagent. This is the preferred ratio of volume of reagent in solution to volume of test solution absorbed as previously described, and results in a highly accurate, precise indicator device of the invention.

Figure 4A:
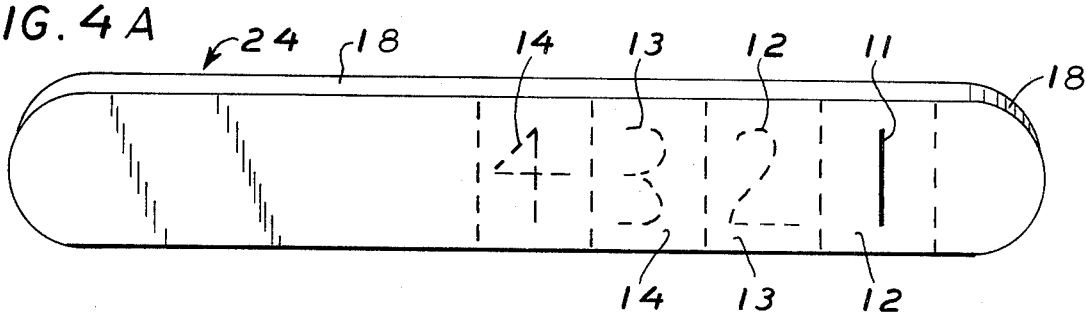
FIGS. 4a, 4b, 4c and 4d are isometric view of an alternate indicator embodiment of the invention showing the possible indicia registrations after immersion in various chemical substances containing solutions.

FIGS. 4a, 4b, 4c and 4d illustrate still another embodiment of the invention. The indicator device is referred to generally by the numeral 24 in these Figures. In FIG. 4a, indicator 24 is shown to comprise a support member 18 as described previously, but bearing reagents 11, 12, 13 and 14 as previously described in a sequence so that reagent 11 is disposed in the form of a symbol 1, reagent 12 is disposed in the form of a symbol 2 and is also disposed in a zone surrounding the symbol 1 formed by a reagent 11. In a similar manner reagent 13 is disposed in the form of a symbol 3 and also in the zone surrounding the symbol 2. Reagent 14 is disposed in the form of a symbol 4 and also in the zone surrounding the symbol 3. In this embodiment, exposure to a chemical containing solution of a specific level will indicate numerically the minimum concentration of chemical in the tested solution and will obliterate numeral symbols for any lower concentrations of chemical. For example, FIG. 4a shows by broken lines the zones and disposition into indicia of the reagent compositions 12, 13 and 14 not registering the specific concentrations of chemical to which they are sensitive. The numeral 1 appears in bold outline as indicative of a "1" concentration of chemical, meaning the indicator 24 as shown in FIG. 4a has been exposed to a solution containing at least 0.2% of chemical.

Figure 4B:
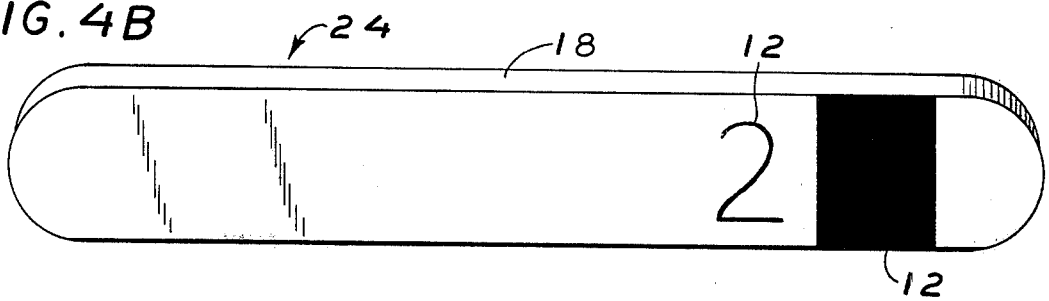
Figure 4C:
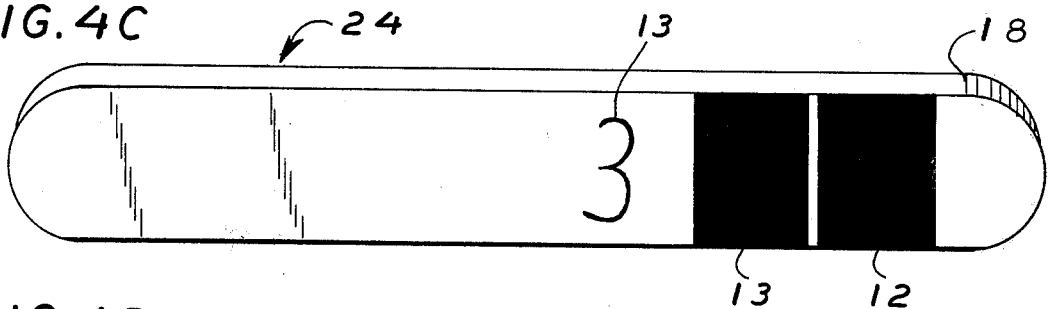
Figure 4D:
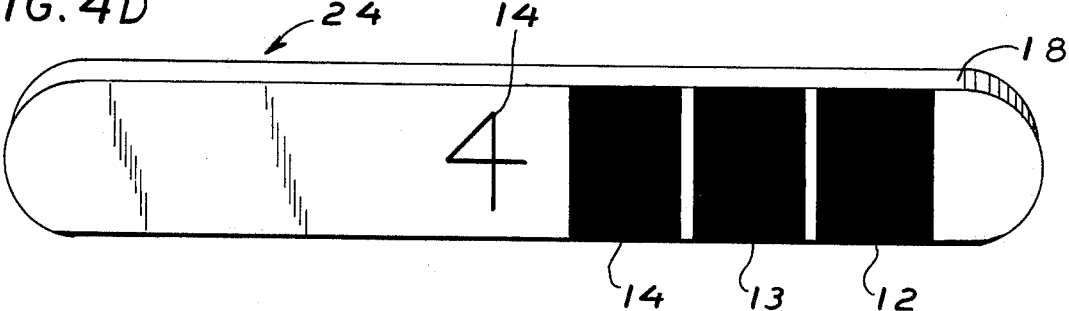

Referring to FIG. 4b, there is seen the registration obtained by immersion, briefly, of indicator device 24 in a test solution containing between 0.3% and 0.4% chemical concentration. The registration of the numeral 2 and obliteration of the also developed numeral 1. This is a clear indication to the user of a "plus 2" concentration in the tested solution. FIG. 4c shows the indicia registered when indicator 24 was immersed in a solution containing between 0.4% and 0.5% chemical and FIG. 4d shows the indicia registered upon immersion of indicator 24 in a solution containing more than 0.5% chemical, i.e.; a "plus 4" reading.

FIG. 5 is an isometric view of a preferred indicator of the invention shown after use by immersion in a solution containing between 0.3% and 0.4% chemical. The indicator 26 comprises as a support member a bibulous material 30 which has been laminated to a strip 32 of stiff supporting material such as polymeric plastic for example a strip of polyethylene, polypropylene or like polymeric material. Apertures 35, 36, 37 and 38 have been cut into supporting strip 32 in the form of positive signals in those areas overlying support member 30 which have been impregnated with the various reagents 11, 12, 13 and 14 previously described. In this manner, the various zones of support member 30 bearing reagents 11, 12, 13 and 14 are viewed through the corresponding apertures 35, 36, 37 and 38 respectively. In addition, an area or zone of support member 30 has also been impregnated with a reagent 9 which is sensitive to an acid pH. The reagent 9 impregnated zone of support member 30 is visible through aperture 39 cut into strip 32. The purpose of the zone impregnated with reagent 9 is to serve as a control. When the indicator 26 is immersed in acid biological fluids, contact of the fluid with reagent 9 registers a color change. The user is then assured that all of the reagent zones below reagent 9 on member 30 have made contact with the solution, and therefore reagents 11, 12, 13 and 14 have been exposed to the fluid specimen.

FIG. 6 is a cross-sectional view along lines 6—6 of FIG. 5 and shows in greater detail the mounting of support member 30 beneath the cutaway zones 35, 36, 37, 38 and 39 in rigid supporting strip 32. This embodiment, as illustrated in FIGS. 5 and 6, immediately provides the user, upon immersion in a fluid specimen, with a visual indication of chemical level registered in terms of plus units which are readily calculated by counting the darkened indicia. Thus the illustrated device of FIGS. 5 and 6 has registered a "plus 3" value of chemical concentration, in the illustration.

FIG. 7 is a view in perspective of another indicator embodiment of the invention which is particularly useful for precise determinations of the concentration of a substance dissolved in liquids, which potentially may have a broad rang of possible concentrations. For example, the indicator shown generally by the numeral 70 is useful in measuring the cholesterol concentration of mammalian blood specimens. Indicator 70 comprises a transparent or highly translucent support member 72 such as a sheet of transparent cellulose acetate, a film of polyethylene, transparentized paper or like materials. Disposed on member 72 are a variety of reagents, such as reagents 11, 12, 13 and 14 previously described, with reagent compositions of intermediate sensitivities disposed between them as illustrated in the figure. Prior to exposure to a solution of cholesterol, for example blood serum, the zones covered by the various reagent compositions are relatively colorless. A sample of blood serum is wiped over the surface of the reagent bearing member 72, causing those reagents which indicate at the level of cholesterol concentration found in the blood specimen to undergo a visible color change. The indicator 70 is "read" by a hand held optical aid or by inserting it in a light projector with a reticule 75. Reticule 75 projects a reference grid, which is superimposed by projection over the indicator 70, whereby the indication registered on 70 is readily observed in a magnified and projected image. Of course when the indicator is to be read directly without the aid of a light projector, there is no need for a transparent support member 72.

The embodiment of the invention described above in relation to FIG. 7 is representative of another facet of the invention which comprises the use of reading aids, such as optical and electromechanical devices to assist in reading the indicators of the invention. More specifically the indicators of the invention function basically by the development of a color change, darkening or opacifying of a zone upon the support member component of the indicator device. Reading of the device is dependent upon an observation of a particular quantity of reacted or indicated zones. The actual "reading" of the indicators can therefore be performed mechanically by instruments designed to count symbols through the use of lenses, mirrors, filters, projectors, detectors and the like which can discriminate by means of light transmission, light reflectance, light scattering, electrical conductivity, radioactivity, etc. Thus, the reading of the indicator devices of the inventor may be carried out mechanically with the aid of photo scanners and like devices. This facet of the invention is particularly advantageous for use of the indicator devices of the invention bearing a large number of different reagent zones, each zone being of a microdot dimension or some dimension not readily observable with the naked eye. Such devices are particularly advantageous in that they use a minimum of reagent material, are fairly compact and can provide readings of great accuracy over wide ranges of possible substance concentrations in the solutions being tested.

The indicators of the invention may be used in ways not limited to those described in the foregoing. For example, before or after exposure to the test specimen, they may be exposed to reagents not previously incorporated in the reactive zones, or to a drying process, e.g. application of heat, or other chemical or physical agents selected for the purpose of developing or enhancing the appearance of visual or otherwise detectable indications.

What is claimed is:

1. An indicator for the measurement of ketones dissolved in biological fluids, which comprises;
    a support member; and
    a plurality of indicating reagents for said ketones, each of which is located in a separate zone of said member and at least two of which indicate the presence of a different concentration of said ketones in solution.

2. The indicator of claim 1 wherein said support member is hydrophobic and said zones are formed of bibulous material.

3. The indicator of claim 1 wherein said reagents are disposed upon said support member in the shape of numerals corresponding to indicia for the level of substance for which they indicate.

4. An indicator for the measurement of albumin dissolved in biological fluids, which comprises:
   a support member; and
   a plurality of indicating reagents for said albumin, each of which is located in a separate zone of said member and at least two of which indicate the presence of a different concentration of said albumin in solution.

5. The indicator of claim 4 wherein said support member is hydrophobic and said zones are formed of bibulous material.

6. An indicator for the measurement of proteins dissolved in biological fluids, which comprises:
   a support member; and
   a plurality of indicating reagents for said protein, each of which is located in a separate zone of said member and at least two of which indicate the presence of a different concentration of said protein in solution.

7. The indicator of claim 6 wherein said support member is hydrophobic and said zones are formed of bibulous material.

8. An indicator for the measurement of uric acid dissolved in biological fluids, which comprises;
   a support member; and
   a plurality of indicating reagents for said uric acid, each of which is located in a separate zone of said member and at least two of which indicate the presence of a difference concentration of said uric acid in solution.

9. The indicator of claim 8 wherein said support member is hydrophobic and said zones are formed of bibulous material.

* * * * *

UNITED STATES PATENT OFFICE
CERTIFICATE OF CORRECTION

PATENT NO. : 4,059,407
DATED : November 22, 1977
INVENTOR(S) : Harry T. Hochstrasser It is certified that error appears in the above-identified patent and that said Letters Patent are hereby corrected as shown below:

Column 6, line 65, The following should be inserted --

Scheme II  Compositions of reagents that effect a titration of the analyte against a chemical oxidant. --

Column 7, line 30, - "Ketones **" should be -- Ketones * --

Column 13, line 3, - "1" should be -- "plus 1" --

Column 13, line 28, - "signals" should be -- signs --

Column 13, line 55, - "plus 3" should be -- "plus 2" --

Column 13, line 61, - "rang" should be -- range --

Signed and Sealed this

Fourteenth Day of March 1978

[SEAL]

Attest:

RUTH C. MASON
*Attesting Officer*

LUTRELLE F. PARKER
*Acting Commissioner of Patents and Trademarks*